(12) United States Patent
Royzen

(10) Patent No.: US 9,032,975 B2
(45) Date of Patent: May 19, 2015

(54) DENTAL DEVICE

(71) Applicant: Michael Royzen, Seattle, WA (US)

(72) Inventor: Michael Royzen, Seattle, WA (US)

( * ) Notice: Subject to any disclaimer, the term of this patent is extended or adjusted under 35 U.S.C. 154(b) by 2 days.

(21) Appl. No.: 14/292,762

(22) Filed: May 30, 2014

(65) Prior Publication Data

US 2014/0261531 A1    Sep. 18, 2014

Related U.S. Application Data

(63) Continuation-in-part of application No. 13/200,838, filed on Oct. 4, 2011, now Pat. No. 8,776,807.

(51) Int. Cl.
*A61C 15/00* (2006.01)
*A61C 15/02* (2006.01)
*A61C 15/04* (2006.01)
*A46B 15/00* (2006.01)

(52) U.S. Cl.
CPC .................. *A61C 15/00* (2013.01); *A61C 15/02* (2013.01); *A61C 15/046* (2013.01); *A46B 15/0073* (2013.01)

(58) Field of Classification Search
CPC ...................................................... A61C 15/00
USPC ............ 132/321, 329, 323, 309, 308; 401/85, 401/86, 89
See application file for complete search history.

(56) References Cited

U.S. PATENT DOCUMENTS

| | | | | |
|---|---|---|---|---|
| 682,892 A * | 9/1901 | Thurston | | 132/328 |
| 940,797 A * | 11/1909 | Fraser | | 401/96 |
| 1,506,417 A * | 8/1924 | Donals | | 132/309 |
| 2,414,245 A * | 1/1947 | Rudd | | 401/89 |
| 4,915,234 A * | 4/1990 | Boeller | | 206/581 |
| 5,975,901 A * | 11/1999 | Kennedy | | 433/141 |
| 6,247,477 B1 * | 6/2001 | Wagner | | 132/309 |
| D475,085 S * | 5/2003 | Whitehorn | | D19/36 |
| 6,568,529 B2 * | 5/2003 | McMurrey | | 206/385 |

* cited by examiner

*Primary Examiner* — Robyn Doan

(57) ABSTRACT

A dental device having a cap and a set of disposable cleaning instruments a user needs for a day or a trip. Each instrument comprising a handle and a portion for cleaning teeth, such as a toothbrush with toothpaste, or a dental flosser, or a toothpick and a handle, or a rupturable dispenser with mouthwash liquid. Each handle and a cap has identical longitudinal cavity with the one open. A part of the first instrument including its cleaning portion is inserted into the cavity of the cap, a part of the second instrument including its cleaning portion is inserted into the cavity of the first instrument, a part of the third instrument including its cleaning portion is inserted into the cavity of the second instrument, and so on. Each cavity and a portion of the instrument inserted into it have at least one set of complementary shapes providing releasable snaps sealing the cavity and holding the engaged instruments and the first instrument and the cap. The device is safe, user friendly and sanitary to carry. Users can assemble the devices with needed type and quantity of instruments for a day or a trip.

7 Claims, 6 Drawing Sheets

DENTAL DEVICE

This application is continuation-in-part of utility patent application Ser. No. 13/200,838 filed on Oct. 4, 2011.

BACKGROUND OF THE INVENTION this invention relates to disposable toothpicks, dental floss and toothbrushes for cleaning teeth and removing plaque.

Toothpicks are beneficial dental devices. They are small and easy to carry. However, when they are carried unprotected in the pocket, they become dirty and are not sanitary. Because toothpicks are sharply pointed objects, they could penetrate the user's clothing and could cause discomfort or pain to the user when they engage the adjoining body portion or skin.

According to U.S. Pat. No. 4,040,433 to Edison, U.S. Pat. No. 5,076,301 to Sulskis, U.S. Pat. No. 6,418,940 to Tcherny, toothpicks are enclosed in protective sanitary containers.

According to U.S. Pat. No. 4,800,905 to Stuart, the toothpick case used as a handle. However, after taking out a toothpick from the case, it is necessary to mount the toothpick to the case in order to use the case as a handle.

Known sanitary containers storing more than one toothpick could be easily contaminated during taking out of the container even the very first toothpick, especially, when the user has no possibility to wash his or her hands before doing it. A toothpick which is taken out could be contaminated as well.

There are known combinations of toothpicks and dental floss, for example U.S. Pat. Application No. 2006/0070636 to Peters describes a toothpick with a length of dental floss wound around it. Most of such devices need sanitary cases to protect both toothpick and dental floss.

According to U.S. Pat. No. 5,915,392 to Isaac, the described combination of a toothpick and dental floss holds the floss inside the toothpick. However, the toothpick itself needs a sanitary container. The toothpick has a perforated area or break point near its middle. When the toothpick is broken a useable length of dental floss is exposed, however, the surfaces of the broken ends are not safe especially for children users because the may result in pricking the user's face, his or her mouth or hands.

According to U.S. Pat. No. 5,174,314 to Charatan and to U.S. Pat. No. 4,403,625 to Sanders, the described devices contain floss in housings with pointed ends to be used as toothpicks. However, the housings if they are used as toothpicks need sanitary containers. In order to release the floss, the parts of the housing should be separated. The patents teach to clean teeth with floss attached to parts with pointed ends which is not safe especially for children users because it may result in pricking the user's face or his or her mouth.

According to U.S. Pat. No. 7,182,542 to Douglas Hohlbein, the described disposable device includes a toothbrush with portion of gel, a handle with one end pointed to be used as a toothpick. The device needs a sanitary container. When the toothpick is used, the toothbrush could be contaminated and vice versa.

According to U.S. Pat. No. 5,975,901 to Joseph H. Kennedy, the described combination toothpick holder and toothpick has handle 12 made as a tube in which a plurality of toothpick ends 14 are inserted, stored and used. After a toothpick 14 is used, it is removed from end 18 and reinserted in end 20. When all of the toothpicks 14 have been used, they are removed from handle 12, cleaned and reinserted, or completely replace with a new unused refill package of toothpicks. The handle 12 holds and supports toothpicks 14. The toothpick's base 26 has a cavity called groove 30 which has larger diameter than base 28 of the adjacent toothpick inserted into the groove as described in the disclosure and shown in the FIG. 3. There is no any connection and, therefore, nor any holding force between the base 28 and the groove 30. The groove 30 is made to nest the base 28 inside it, but it does not hold the base 28. The toothpicks 14 are stacked inside the tubular handle and are held by the handle. The toothpicks do not hold each other and will fall apart without the holder/handle 12. The holder/handle 12 not only complicates the device but also brings sanitary problems. The used toothpick cannot be discarded after its use. They have to be inserted in the other end of the holder/handle 12. By inserting a used toothpick at one end of the tubular holder-handle, a user pushes all toothpicks in the tube forward exposing a clean toothpick at the other end of the holder/handle 12. The need to push all toothpicks inside the holder/handle 12 every time to expose a clean toothpick complicates the use of the device. Another disadvantage is the need keep all dirty used toothpicks inserted back into the holder/handle until all toothpicks are used. The used toothpicks stored in the holder/handle become incubators for bacteria and mold that spread everywhere inside the holder/handle tube and inhaled by the user of the device while cleaning teeth with a clean toothpick. Also, there is a danger that a used toothpick can be used again when all toothpicks in the holder/handle are used and the user did not pay attention to the last clean toothpick has been used.

Many users especially users with braces correcting the position of their teeth are recommended to clean their teeth and braces after each meal. They need to use disposable dental devices, however, existing disposable dental devices are not safe enough, sanitary and attractive.

SUMMARY OF THE INVENTION

The objective of the present invention is to provide a disposable dental device suitable for safe, convenient and sanitary use. Another objective of the invention is to make a dental device more attractive for users. Another objective of the invention is to provide a single device which allow taking all dental care instruments a user needs for a day including toothpicks, dental flossers, toothbrushes with toothpaste. Another objective of the invention is to make possible the users to assemble the devices with needed type and quantity of dental instruments for a day or a trip.

The present invention of a dental device provides at least two or three disposable cleaning instruments and a cap. Each cleaning instrument comprising a portion for cleaning teeth attached to the handle. A cleaning portion can be made as a toothpick, or toothbrush with gel or toothpaste, or a length of dental floss, or a flosser, or a rupturable dispenser with mouthwash liquid. The device can be assembled with comprising instruments with the same or different cleaning portions. Each handle has a longitudinal cavity with the one end adjacent to the cleaning portion closed and with the other end open. The cap has the same cavity as each handle.

A part of the first instrument including at least its cleaning portion is inserted into the cavity of the cap. A part of the second instrument including at least its cleaning portion is inserted into the cavity of the first cleaning instrument. If there are three instruments, a part of the third instrument including at least its cleaning portion is inserted into the cavity of the second cleaning instrument. And so on, if there are more instruments. Each said cavity and a portion of the instrument inserted into it have at least one set of complementary shapes providing releasable snap sealing the cavity and holding the engaged instruments and the first instrument and the cap. The device can comprise instruments with the same or different cleaning portions.

In another embodiment, the handles are made of different colors.

In another embodiment, handles of different instruments have different colors.

In another embodiment, a dental device in which instrument is a dental flosser having a piece of dental floss and a holder, the ends of the floss are attached to the holder and the holder is attached to the handle. At least a part of the holders is made elastic and bent while inserted in said cavity with ability to spring back after removing the flosser from said cavity.

In another embodiment, a toothpick and its handle is made as a single piece body. A part of another instrument including at least its cleaning portion can be inserted into the cavity of the handle.

In another embodiment, a toothbrush and its handle is made as a single piece body. A part of another instrument including at least its cleaning portion can be inserted into the cavity of the handle.

In another embodiment, the holder of the flosser its handle is made as a single piece body. A part of another instrument including at least its cleaning portion can be inserted into the cavity of the handle.

DETAILED DESCRIPTION OF THE PREFERRED EMBODIMENT

Figure 1:
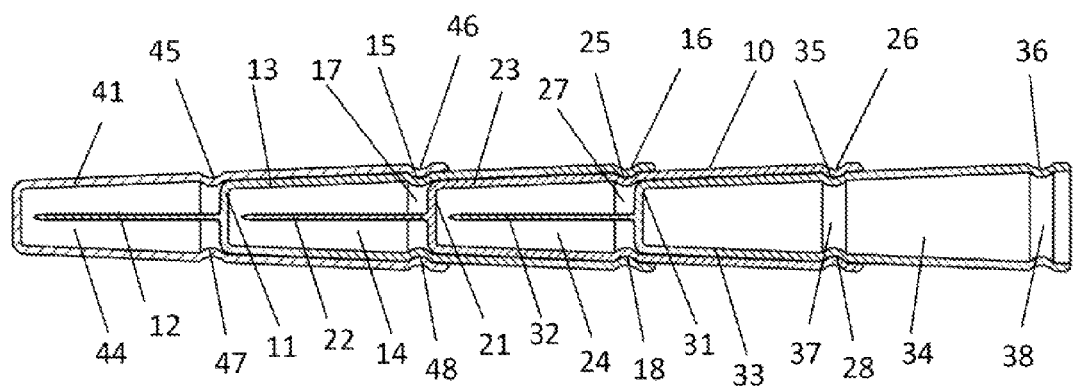
FIG. 1 shows a longitudinal cross section of the dental device having three disposable toothpick instruments.
Figure 2:
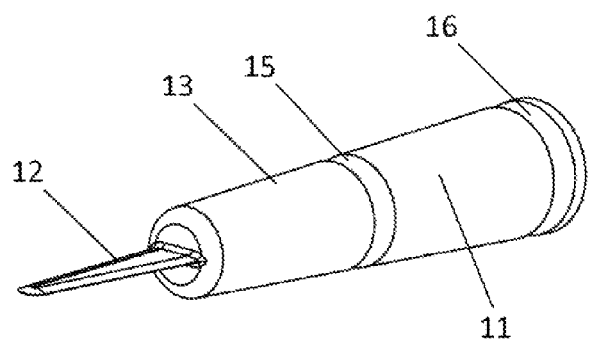
FIG. 2 depicts a disposable toothpick instrument.

FIG. 1 shows a longitudinal cross section of the dental device 10 comprising three identical disposable toothpick instruments 11, 21 and 31 and a cap 41. FIG. 2 depicts a disposable toothpick instrument 11.

Each cleaning instrument comprising a portion for cleaning teeth made as a toothpick and a handle. The instrument 11 has a toothpick 12 attached to the handle 13. The instrument 21 has a toothpick 22 attached to the handle 23. The instrument 31 has a toothpick 32 attached to the handle 33. Each handle has a longitudinal cavity with the one end adjacent to the cleaning portion closed and with the other end open. Instrument 11 has a cavity 14, instrument 21 has a cavity 24 and instrument 31 has a cavity 34. The cap 41 has the identical cavity 44. A part of the instrument 11 including its toothpick 12 is inserted into the cavity 44 of the cap 41. A part of the instrument 21 including its toothpick 22 is inserted into the cavity 14 of the instrument 11. A part of the instrument 31 including its toothpick 32 is inserted into the cavity 24 of the instrument 21.

Each instrument and the cap 41 have two grooves on the outside surface. The instrument 11 has groves 15 and 16. The instrument 21 has groves 25 and 26. The instrument 31 has groves 35 and 36. The cap 41 has groves 45 and 46. The snap grooves are grooves are 15, 25 and 35.

Each cavity inside has a complementary shape as snap protrusions, providing releasable snaps sealing the toothpick and holding the inserted instrument.

The cavity 14 has bulges 17 and 18. The cavity 24 has bulges 27 and 28. The cavity 34 has bulges 37 and 38. The cavity 44 has bulges 47 and 48.

The bulge 48 is releasably snapped into the grove 15. The bulge 18 is releasably snapped into the grove 25. The bulge 28 is releasably snapped into the grove 35.

Each set of snapped shapes provide releasable sealing of the toothpicks and holding the engaged instruments or the first instrument and the cap. The handles 13, 23 and 33 can be made of different colors. The instrument 11 can be made as a single piece object.

The device can be used in the following ways. The user of the device releases instrument 31 first, then uses instrument 21, and then 11. However, the user of the device can release any instrument for use. A used instrument is discarded. In order to use instrument 11 first, it is necessary to remove the cap 41. The cap 41 can be temporarily inserted into the cavity 34 and bulge 38 is releasably snapped into the grove 45. The handles of instrument 11, 21 and 31 can be used as a single handle for toothpick 12. Also, the instrument 11 can be removed to use it separately. In both ways, the instrument 11 is discarded after its use and the cap is inserted to seal instrument 21 by snapping the bulge 48 into the grove 25. The user can start with instrument 21 as well and this case is similar to the use of the instrument 11.

Figure 3:
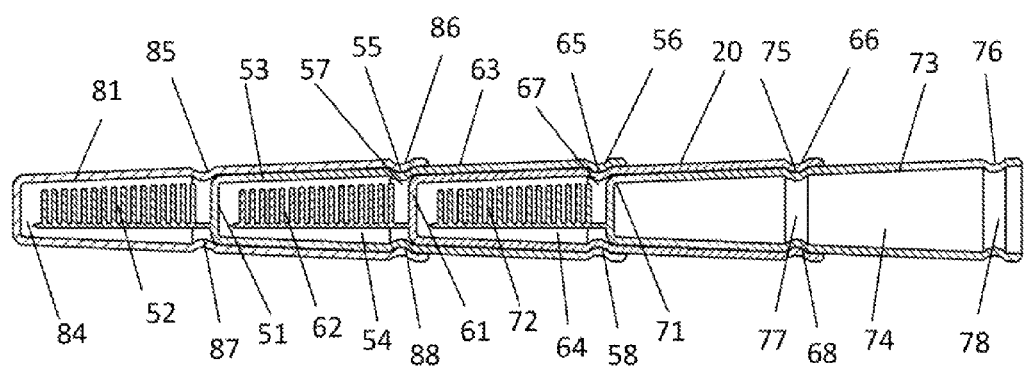
FIG. 3 shows a longitudinal cross section of a dental device having three disposable toothbrush instruments.

FIG. 3 shows a longitudinal cross section of the dental device 20 comprising three identical disposable toothbrush instruments 51, 61 and 71 and a cap 81.

Each cleaning instrument comprising a portion for cleaning teeth made as a toothbrush and a handle. The instrument 51 has a toothbrush 52 attached to the handle 53. The instrument 61 has a toothbrush 62 attached to the handle 63. The instrument 71 has a toothbrush 72 attached to the handle 73. Each handle has a longitudinal cavity with the one end adjacent to the cleaning portion closed and with the other end open. The instrument 51 has a cavity 54, the instrument 61 has a cavity 64 and the instrument 71 has a cavity 74. The cap 81 has the identical cavity 84. A part of the instrument 51 including its toothbrush 52 is inserted into the cavity 84 of the cap 81. A part of the instrument 61 including its toothbrush 62 is inserted into the cavity 54 of the instrument 51. A part of the instrument 71 including its toothbrush 72 is inserted into the cavity 64 of the instrument 61. Each instrument and the cap 81 have two grooves on the outside surface. The instrument 51 has groves 55 and 56. The instrument 61 has groves 65 and 66. The instrument 71 has groves 75 and 76. The cap 81 has groves 85 and 86.

The cavity 54 has bulges 57 and 58. The cavity 64 has bulges 67 and 68. The cavity 74 has bulges 77 and 78. The cavity 84 has bulges 87 and 88.

The bulge 88 is releasably snapped into the grove 55. The bulge 58 is releasably snapped into the grove 65. The bulge 68 is releasably snapped into the grove 85.

Each set of snapped shapes provide releasable sealing of the toothbrushes and holding the engaged instruments and the first instrument and the cap.

The handles 53, 63 and 73 can be made of different colors. The instrument 51 can be made as a single piece object.

Figure 4:
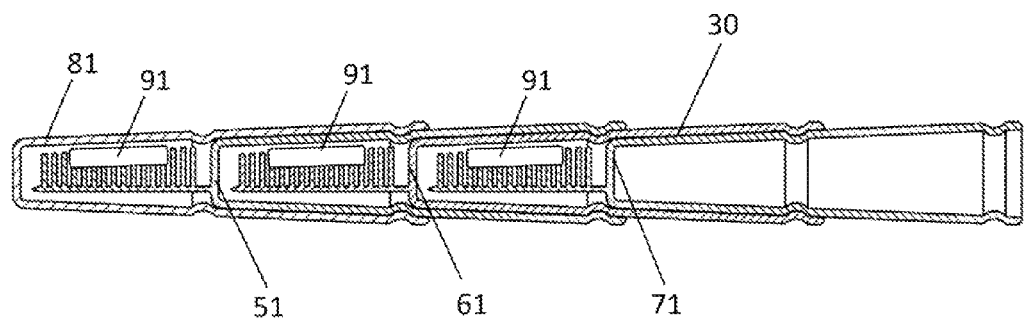
FIG. 4 shows a longitudinal cross section of a dental device having three disposable toothbrush instruments with toothpaste.
Figure 5:
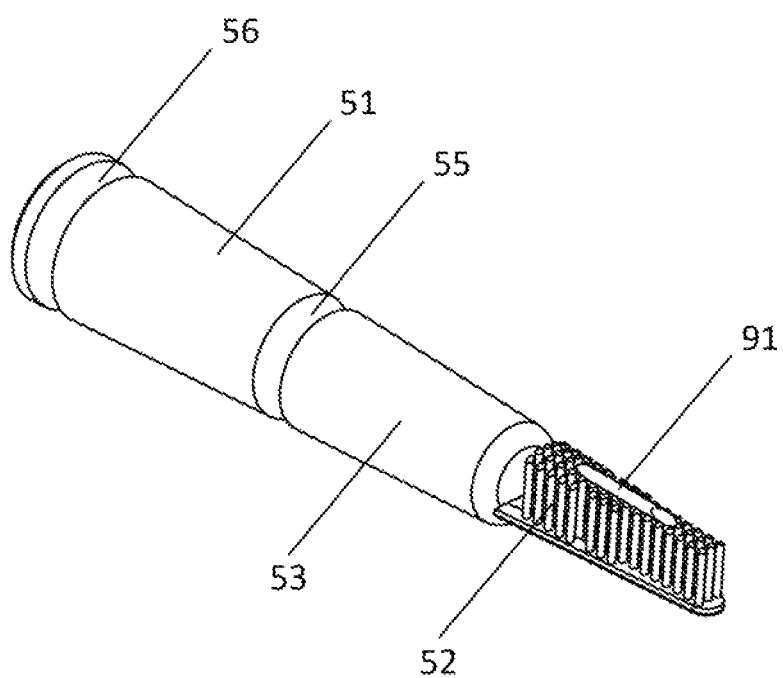
FIG. 5 depicts a toothbrush instrument.

FIG. 4 shows a longitudinal cross section of a dental device 30 having three identical disposable toothbrush instruments 51, 61, and 71, each with a quantity of toothpaste or gel 91. FIG. 5 depicts a disposable toothbrush instrument 51 with a quantity of toothpaste 91. It also can be a quantity of toothpowder or a gel.

The device 20 and 30 can be used in the following ways. The user of the device releases instrument 71 first, then uses instrument 61, and then 51. However, the user of the device can release any instrument for use. A used instrument is discarded. In order to use instrument 51 first, it is necessary to remove the cap 81. The cap 81 can be temporarily inserted into the cavity 74 and bulge 78 is releasably snapped into the grove 85. In one way, the handles of instrument 51, 61 and 71 are used as a single handle for toothbrush 52. In another way, the instrument 51 is removed to use it separately. In both ways, the instrument 51 is discarded after its use and the cap 81 is inserted to seal instrument 61 by snapping the bulge 88 into the grove 75. The user can start with instrument 71 as well and this case is similar to the use of the instrument 51.

Figure 6:
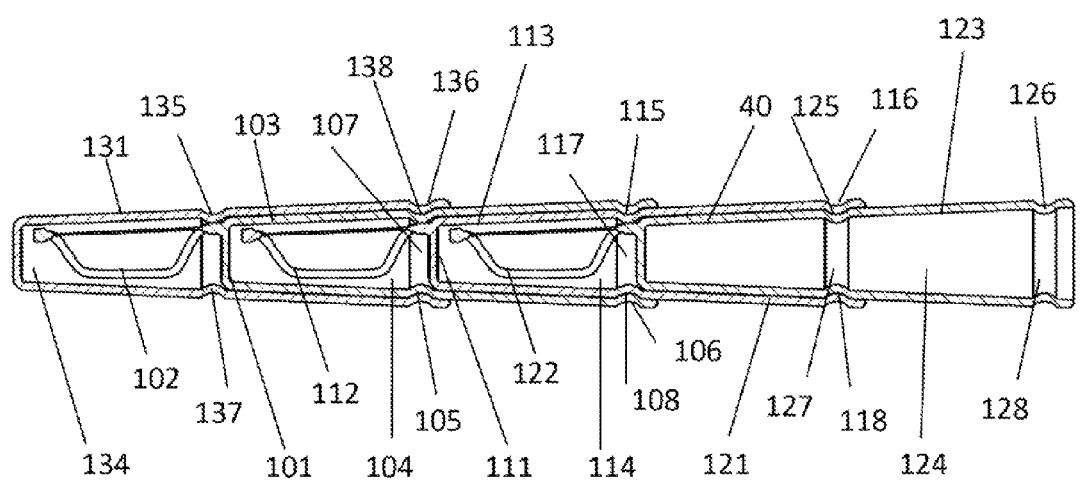
FIG. 6 shows a longitudinal cross section of a dental device having three disposable dental flosser instruments.

FIG. 6 shows a longitudinal cross section of a dental device 40 having three identical disposable dental flosser instruments 101, 111 and 121 and a cap 131.

Each instrument comprising a flosser and a handle. The instrument 101 has a flosser 102 attached to the handle 103. The instrument 111 has a flosser 112 attached to the handle 113. The instrument 121 has a flosser 122 attached to the handle 123. Each handle has a longitudinal cavity with the one end adjacent to the cleaning portion closed and with the other end open. The instrument 101 has a cavity 104, the instrument 111 has a cavity 114 and the instrument 121 has a cavity 124. The cap 131 has the identical cavity 134. A part of the instrument 101 including its flosser 102 is inserted into the cavity 134 of the cap 131. A part of the instrument 111 including its flosser 112 is inserted into the cavity 104 of the instrument 101. A part of the instrument 121 including its flosser 122 is inserted into the cavity 114 of the instrument 111. Each instrument and the cap 131 have two grooves on the outside surface. The instrument 101 has groves 105 and 106. The instrument 111 has groves 115 and 116. The instrument 121 has groves 125 and 126. The cap 131 has groves 135 and 136.

The cavity 104 has bulges 107 and 108. The cavity 114 has bulges 117 and 118. The cavity 124 has bulges 127 and 128. The cavity 134 has bulges 137 and 138.

The bulge 138 is releasably snapped into the grove 105. The bulge 108 is releasably snapped into the grove 115. The bulge 118 is releasably snapped into the grove 135.

Each set of snapped shapes provide releasable sealing of the flosser and holding the engaged instruments and the first instrument and the cap. The flossers 102, 112 and 122 are shown bent went they are inserted into the cavities. The handles 103, 113 and 123 can be made of different colors.

Figure 7:
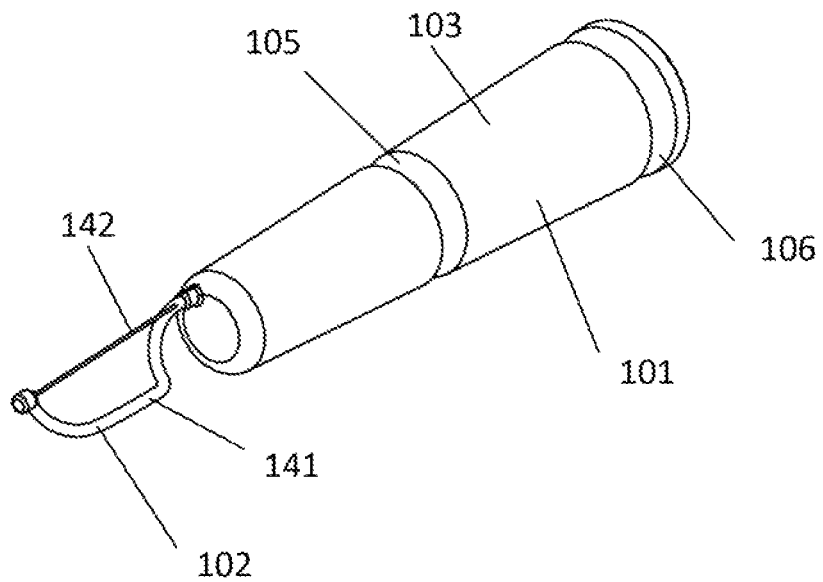
FIG. 7 depicts a dental flosser instrument with the flosser shown bent as it bent when it is inserted into the cavity of another instrument (not shown).
Figure 8:
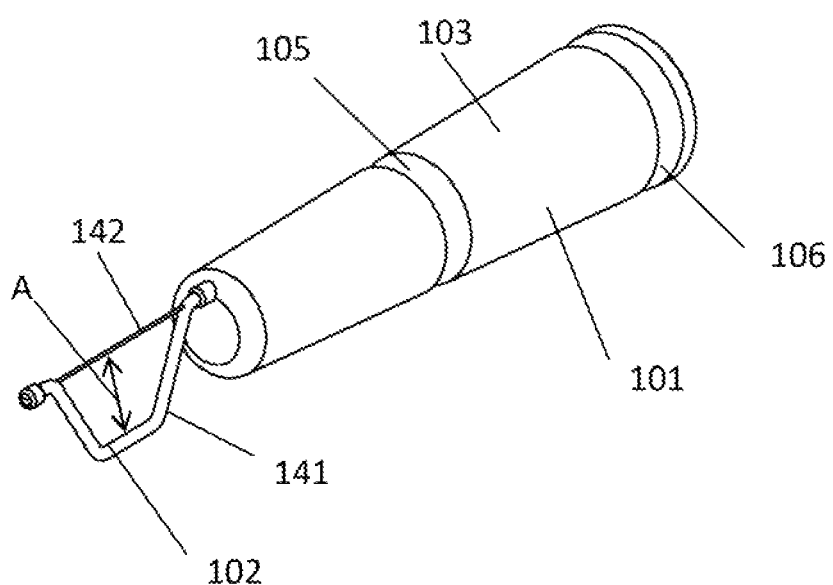
FIG. 8 depicts a dental flosser instrument with the flosser shown unbent when it is released.

FIG. 7 depicts a dental flosser instrument 101 with the flosser 102 shown bent as it bent when it is inserted into the cavity of another instrument (not shown). FIG. 8 depicts a dental flosser instrument 101 with the flosser 102 shown unbent when it is released.

The flosser 102 has a holder 141 and a piece of dental floss 142 attached to the holder 141. The size A for can be 8-15 mm. The size of the cavity to accommodate the flosser has to be corresponding. However, it is possible to reduce the size of the cavity by bending the holder 141 as it is shown on FIG. 7. After releasing the flosser 102, the holder 141 springs back and restores its shape with needed size A as it is shown on FIG. 8. The handle 103 and the holder 141 can be made as a single piece object. The instrument 101 can be made as a single piece object. The bendable holder 141 can be made of springing material.

The device 40 can be used in the following ways. Preferably, the user of the device releases instrument 121 first, then uses instrument 111, and then 101. If the holders are not bent when inserted into their respective cavities, the user of the device can start from any instrument. A used instrument is discarded.

Figure 9:
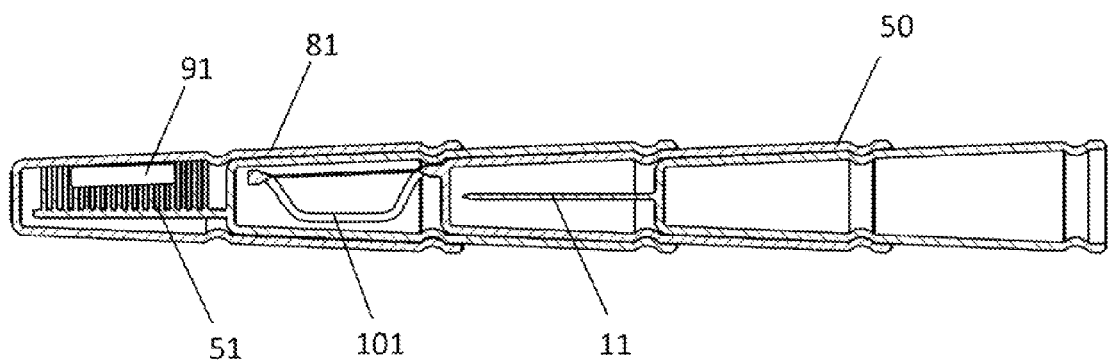
FIG. 9 shows a longitudinal cross section of a dental device having disposable toothbrush instrument, disposable dental flosser instrument and disposable toothpick instrument. All drawings are magnified.

FIG. 9 shows a longitudinal cross section of a dental device 50 having the disposable toothbrush instrument 51 with toothpaste 91, the disposable dental flosser instrument 101, the disposable toothpick instrument 11 and the cap 81. Preferably, the user of the device releases the instrument 11 first, then uses the instrument 101, and then uses the instrument 51. If the holder of the flosser is not bent when inserted into the cavity, the user of the device can start from any instrument. A used instrument is discarded. The instruments 51, 101 and 11 can be made of different colors.

Material that can be used to make the disposable instruments include nylon, polymers, polyethylene, polypropylene and other materials well known to those of skill in the art.

The dental device is attractive, safe, user friendly and sanitary to carry. Many users, especially those who wear braces, have to clean teeth after each meal including snacks. A single device allow taking all dental care instruments a user needs for a day including toothpicks, dental flossers, toothbrushes with toothpaste. The devices can be preassembled. Also, users can assemble the devices with needed type and quantity of dental instruments for a day or a trip and place them in the order they are used.

What is claimed is:

1. A dental cleaning assembly comprising at least first, second, third disposable cleaning instruments and a cap, each of the disposable cleaning instruments comprising a teeth cleaning portion and a handle portion, wherein the handle having outer and inner surfaces and a longitudinal cavity formed therein, said cavity including a closed end which is adjacent to the teeth cleaning portion, an intermediate portion and an open end; said handle having first and second circumferentially extending grooves on said outer surface and first and second bulges on said interior surface, said first groove being on the outer surface of said intermediate portion and said second groove located on the outer surface of said open end, said first bulge extending from said interior surface of the intermediate portion and said second bulge extending from said interior surface of said open end, said cap including an outer surface with two circumferentially extending grooves and a longitudinal cavity formed from an interior surface, wherein said interior surface comprising two bulges, said cavity having a closed end, an intermediate portion and an open end; one of said grooves and one of said bulges extending from the outer and inner surfaces of the intermediate portion of the cap respectively and the other of said grooves and the other of said bulges extending from the outer and inner surfaces of the open end of the cap respectively, the disposable cleaning instruments and the cap being releasably coupled to each other in a stacked configuration such that said bulge portion of the intermediate portion of said cap sits against the closed end cavity of the first disposable instrument and said bulge portion at the open end of said cap releasably snaps onto said first groove of the first disposable instrument; said closed end of the second disposable instrument abuts against the first bulge of the first disposable instrument and first groove of said second disposable instrument releasably snaps onto the second bulge of the first disposable portion; said closed end of the third disposable instrument abuts against the first bulge of the second disposable instrument and the first groove of the third disposable instrument releasably snaps onto the second bulge of the second disposable instrument and any additional disposable cleaning instrument can be coupled to the previous one in the stacked configuration;

wherein the teeth cleaning portion of each disposable instrument is a toothpick, toothbrush, a toothbrush with gel or toothpaste, a length of dental floss, a dental flosser or a rupturable dispenser with mouthwash liquid, said disposable cleaning instruments having the same or different types of teeth cleaning portions wherein the disposable cleaning instrument being discarded immediately after its use.

2. A dental cleaning assembly according to claim 1 further comprising handle of different colors.

3. A dental cleaning assembly according to claim 1 further comprising the instrument being a dental flosser which includes a piece of dental floss and a holder, ends of dental floss are attached to the holder.

4. A dental cleaning assembly according to claim 3 wherein at least a part of said holder is made elastic.

5. A dental cleaning assembly according to claim 3 wherein the holder of the flosser and its handle being made as a single piece body.

6. A dental cleaning assembly according to claim 1 wherein the toothpick and its handle being made as a single piece body.

7. A dental cleaning assembly according to claim 1 wherein the toothbrush and its handle being made as a single piece body.

* * * * *